United States Patent
Kamenaga et al.

(10) Patent No.: US 10,166,135 B2
(45) Date of Patent: Jan. 1, 2019

(54) POSTURE CORRECTIVE BRACE

(71) Applicant: GIKEN INC., Hatsukaichi (JP)

(72) Inventors: Masanori Kamenaga, Hatsukaichi (JP); Ryosuke Hamamoto, Hatsukaichi (JP)

(73) Assignee: GIKEN INC., Hatsukaichi (JP)

( * ) Notice: Subject to any disclaimer, the term of this patent is extended or adjusted under 35 U.S.C. 154(b) by 590 days.

(21) Appl. No.: 14/745,931

(22) Filed: Jun. 22, 2015

(65) Prior Publication Data
US 2015/0282974 A1    Oct. 8, 2015

Related U.S. Application Data

(63) Continuation of application No. PCT/JP2013/060846, filed on Apr. 10, 2013.

(51) Int. Cl.
*A61F 5/02* (2006.01)
*A61F 5/01* (2006.01)
*A61F 5/03* (2006.01)

(52) U.S. Cl.
CPC ............ *A61F 5/028* (2013.01); *A61F 5/0193* (2013.01); *A61F 5/02* (2013.01); *A61F 5/03* (2013.01)

(58) Field of Classification Search
CPC .......... A61F 5/0193; A61F 5/02; A61F 5/022; A61F 5/024; A61F 5/026; A61F 5/028; A61F 5/03
USPC ........... 602/19; 128/96.1, 99.1, 100.1, 102.1, 128/105.1, 106.1, 107.1
See application file for complete search history.

(56) References Cited

U.S. PATENT DOCUMENTS

| 3,548,817 | A |   | 12/1970 | Mittasch |
| 5,363,863 | A | * | 11/1994 | Lelli ...................... A61F 5/028 128/876 |
| 5,647,824 | A |   | 7/1997 | Levenson |

(Continued)

FOREIGN PATENT DOCUMENTS

| CN | 201481609 U | 5/2010 |
| CN | 202397661 U | 8/2012 |

(Continued)

OTHER PUBLICATIONS

Extended European Search Report dated Oct. 25, 2016, in European Patent Application No. 13881695.4, Total of 5 pages.

(Continued)

*Primary Examiner* — Keri J Nelson
(74) *Attorney, Agent, or Firm* — Tracy M. Heims; Apex Juris, Pllc.

(57) ABSTRACT

A posture corrective brace including a device for correcting asymmetry of the pelvis so as to surround the circumference of the pelvis, and/or a device for correcting asymmetry of the lower part of the thorax attached so as to surround the circumference of the lower part of the thorax, including: the innominate front compression part capable of abutting the abdominal part near the front side of the right or left innominate, and the innominate rear compression part capable of abutting the pelvis near the rear side of the right or left innominate; and/or the thorax front compression part capable of abutting the vicinity of the front side of the lower part of the right or left thorax, and the thorax rear compression part capable of abutting the vicinity of the rear side of the lower part of the right or left thorax.

8 Claims, 4 Drawing Sheets

(56) References Cited

U.S. PATENT DOCUMENTS 6,500,137 B1    12/2002   Robarber
6,964,644 B1    11/2005   Garth

FOREIGN PATENT DOCUMENTS

| CN | 202776661 U | 3/2013 |
|---|---|---|
| CN | 103442669 A | 12/2013 |
| CN | 103598941 A | 2/2014 |
| EP | 0555154 A1 | 8/1993 |
| JP | 026-1589 | 2/1951 |
| JP | H08-89521 A | 4/1996 |
| JP | 09-000553 | 1/1997 |
| JP | 2008-272449 A | 11/2008 |
| JP | 2009-100865 A | 5/2009 |
| JP | 3164201 U | 10/2010 |
| WO | WO2009-054354 A1 | 4/2009 |

OTHER PUBLICATIONS

Office Action and Search Report dated Nov. 1, 2016, in Chinese Patent Application No. 201330030353.X, Total of 6 pages.
English Abstract of WO2009-054354A1, Total of 1 page.
English Abstract of CN103598941A, Total of 1 page.
English Abstract of CN202397661U, Total of 1 page.
English Abstract of CN202776661U, Total of 1 page.
English Abstract of CN201481609U, Total of 1 page.
Japanese Office Action with English translation for 2014-514639.

* cited by examiner

POSTURE CORRECTIVE BRACE

CROSS REFERENCE TO RELATED APPLICATIONS

This is a continuation application of International Patent Application No. PCT/JP2013/060846 filed on Apr. 10, 2013, of which full contents are incorporated herein by reference.

BACKGROUND OF THE INVENTION

Field of the Invention

The present invention relates to a posture corrective brace for correcting pelvic or lower thorax asymmetry.

Description of the Background Art

Low back pain includes pain caused by bones, joints, or muscles, pain caused by diseases of the internal organs, and pain caused by aging. For example, Patent Document 1 discloses a device as a technique of relieving low back pain caused by bones, joints, or muscles. In this technique, a user standing on a base finds a location where substantially no pain is felt on the back, front, and pelvis of the user, and then restrains the pelvis with pressure from a support pad. This technique does not rotate the spine and pelvis around the hip joint but rotates the spine itself and the sacroiliac joint around the pelvis when the user moves his or her back.

PRIOR ART DOCUMENTS

Patent Documents

Patent Document 1: Japanese Patent Application Publication No. 2008-272449

Problems to be Solved

Some low back pain is caused by pelvic asymmetry, e.g., a malalignment between the sacrum and innominates on both sides of the sacrum when one of the bones is tilted. Such a malalignment displaces a sacroiliac joint and causes pain around the sacroiliac joint between the innominates and the sacrum, leading to low back pain. If the overall thorax is made asymmetric by a tilt of the spine, an upward movement of the upper part of the thorax during inhalation or when bending the body backward may move the lower part of the thorax upward with the upper part without laterally opening the lower part. This may apply a load to the pelvis or the lumbar vertebrae so as to cause low back pain.

The device described in Patent Document 1 is a technique of restraining the pelvis with the pressure from a support pad located at a point where the pain of forward bending or backward bending can be substantially relieved. Therefore, a cause of low back pain, e.g., malalignment between the sacrum and innominates on both sides of the sacrum cannot be corrected during active arm and leg exercises requiring a high degree of freedom, e.g., walking and golf swings. Further, the restraining technique is insufficiently effective in symmetrically positioning the pelvis and thorax with reliability.

Further, the device with a base placed on the floor and legs raised from the base has a large size, requiring an installation space. Still further, the used device restrains the body substantially in an upright position in a continuous manner, leading to inconvenience.

SUMMARY OF THE INVENTION

The present invention has been devised in consideration of these problems. An object of the present invention is to provide a small, lightweight, and usable device that can effectively correct the posture, i.e., asymmetry of the pelvis or the lower part of a thorax to a symmetric positional relationship during active arm and leg exercises having a high degree of freedom, e.g., arm swinging, forward and backward bending, walking, squatting, or golf swings.

Means for Solving Problems

Figure 7:
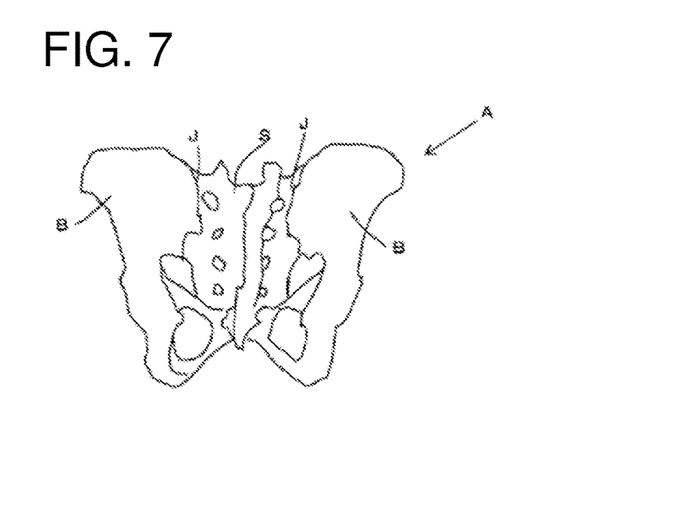
FIG. 7 depicts an explanatory drawing showing the configuration of the pelvis.
Figure 10:
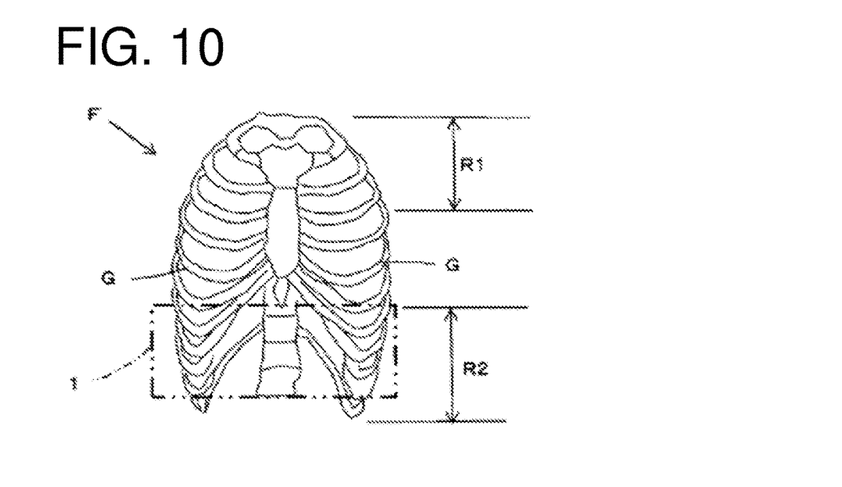
FIG. 10 depicts an explanatory drawing showing the configuration of a thorax.

In the present invention, "internal" means the direction toward the center line of the body and "external" means the direction away from the center line of the body. As shown in FIG. 7, the pelvis A includes a pair of right and left innominates B, the sacrum S, the coccyx, and the pubic symphysis connecting these bones, and the sacroiliac joint J. As shown in FIG. 10, the thorax F includes the right and left ribs G, thoracic vertebra, and sternum.

A posture corrective brace 1 according to the first aspect of the present invention including a device for correcting asymmetry of the pelvis A, the device attaches to the body such that the device surrounds the circumference of the pelvis A of the body, and/or, a device for correcting asymmetry of a lower part of the thorax F, the device attaches to the body such that the device surrounds the circumference of the lower part of the thorax F of the body, the posture corrective brace comprises:

one or a combination of at least two of a four-compression part group consisting of the innominate front compression part 2 capable of abutting an abdominal part near the front side of the right or left innominate B, the innominate rear compression part 3 capable of abutting the pelvis near the rear side of the right or left innominate B, the thorax front compression part 4 capable of abutting the vicinity of the front side of the lower part of the right or left thorax F, and the thorax rear compression part 5 capable of abutting the vicinity of the rear side of the lower part of the right or left thorax F; and at least one body brace 6 attached to the body such that the at least one body brace 6 surrounds the circumference of the body, at least one body brace 6 including the front frame 7 in a substantially belt-like shape laterally extending on the abdominal part of the front side of the body or the lower part of the thorax F, two first belt winding mechanisms 10 vertically disposed on the left end of the front frame 7 on the external side thereof, two second belt winding mechanisms 11 vertically disposed on the right end of the front frame 7 on the external side thereof, and two unstretchable fastening belts 9 each having one end fastened to one of the two first belt winding mechanisms 10 and the other end fastened to one of the two second belt winding mechanisms 11, at least one body brace 6 including two body braces 6 when surrounding two portions as the circumference of the pelvis A of the body and the circumference of the lower part of the thorax F of the body, and including one body brace 6 when surrounding one portion as the circumference of the pelvis A of the body or the circumference of the lower part of the thorax F of the body, wherein the innominate front compression part 2 includes the first front pad 20 disposed on the left end of the front frame 7 on the internal side thereof and the second front pad 21 disposed on the right end of the front frame 7 on the internal side thereof, the first front pad 20 and the second front pad 21 having body contact surfaces each shaped as an inclined surface 24 formed so as to press the front side of the right or left innominate B such that the innominate B can be guided from the forward external side to the backward central side, wherein the innominate rear compression part 3 includes a back frame 8 laterally extended so as to compress the rear portions of the right and left innominates B, the first back pad 30 disposed on the left end of the back frame 8 on the internal side thereof, the second back pad 31 disposed on the right end of the back frame 8 on the internal side thereof, and belt insertion portions 36 configured to allow the two fastening belts 9 to be inserted thereinto vertically and separately, the belt insertion portions 36 disposed at positions on the back frame 8 on the external side thereof interposed between the first back pad 30 and the second back pad 31, the two fastening belts 9 being inserted into the belt insertion portions 36, the first front pad 30 and the second back pad 31 having body contact surfaces each shaped as an inclined surface 34 formed so as to press the rear side of the right or left innominate B such that the innominate B can be guided from the backward external side to the central side, wherein the thorax front compression part 4 includes a third front pad 22 disposed on the left end of the front frame 7 on the internal side thereof and a fourth front pad 23 disposed on the right end of the front frame 7 on the internal side thereof, the third front pad 22 and the fourth front pad 23 having body contact surfaces each shaped as an inclined surface 25 formed so as to press the front side of the right or left rib G such that the rib G can be guided from the forward side to the laterally-extended side, wherein the thorax rear compression part 5 includes a back frame 8 laterally extended so as to compress the rear portions of the right and left ribs G, a third back pad 32 disposed on the left end of the back frame 8 on the internal side thereof, a fourth back pad 33 disposed on the right end of the back frame 8 on the internal side thereof, and belt insertion portions 36 configured to allow the two fastening belts 9 to be inserted thereinto vertically and separately, the belt insertion portions 36 disposed at positions on the back frame 8 on the external side thereof interposed between the third back pad 32 and the fourth back pad 33, the two fastening belts 9 being inserted into the belt insertion portions 36, the third back pad 32 and the fourth back pad 33 having body contact surfaces each shaped as an inclined surface 35 formed so as to press the rear sides of the right and left ribs G inward such that the front sides of the ribs G can be extended laterally, and wherein the body is fastened by the upper side of the first or third front pad 20, 22 and/or the upper side of the first or third back pad 30, 32 on the left side of the body, on a priority basis, when the upper fastening belt 9 of the first belt winding mechanism 10 out of the two fastening belts 9 is operated in a winding direction; the body is fastened by the lower side of the first or third front pad 20, 22 and/or the lower side of the first or third back pad 30, 32 on the left side of the body, on a priority basis, when the lower fastening belt 9 of the first belt winding mechanism 10 out of the two fastening belts 9 is operated in a winding direction; the body is fastened by the upper side of the second or fourth front pad 21, 23 and/or the upper side of the second or fourth back pad 31, 33 on the right side of the body, on a priority basis, when the upper fastening belt 9 of the second belt winding mechanism 11 out of the two fastening belts 9 is operated in a winding direction; and the body is fastened by the lower side of the second or fourth front pad 21, 23 and/or the lower side of the second or fourth back pad 31, 33 on the right side of the body, on a priority basis, when the lower fastening belt 9 of the second belt winding mechanism 11 out of the two fastening belts 9 is operated in a winding direction.

A posture corrective brace 1 according to the second aspect of the present invention, in the first aspect of the present invention, wherein the first belt winding mechanism 10 or the second belt winding mechanism 11 is detachably mounted on the front frame 7.

Advantageous Effects of the Invention

Figure 8:
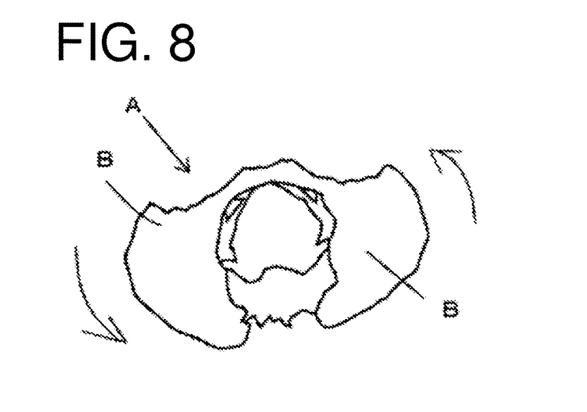
FIG. 8 depicts an explanatory drawing showing pelvic asymmetry.

According to the posture corrective brace 1 of the first aspect of the present invention, as shown in FIG. 8, if the right and left innominates B are rotated and are asymmetrically displaced in the longitudinal direction so as to cause lower-back pain or a displacement between the right and left innominates B and the sacrum S at the center causes asymmetry of the right and left sacroiliac joints J, that is, if the pelvis A has asymmetry, the innominate front compression parts 2 press protrusions on the front sides of the right and left innominates B from the front to the rear and return the innominates B to a symmetrical state so as to correct posture. Moreover, the innominate rear compression parts 3 press the right and left sacroiliac joints J, located at the boundary between the sacrum S and the right and left innominates B, from the outside to the center direction of the body in the lateral direction of the body. This eliminates a malalignment of the innominate B and the sacrum S, i.e., displacement of the sacroiliac joint J, to correct posture.

Figure 11:
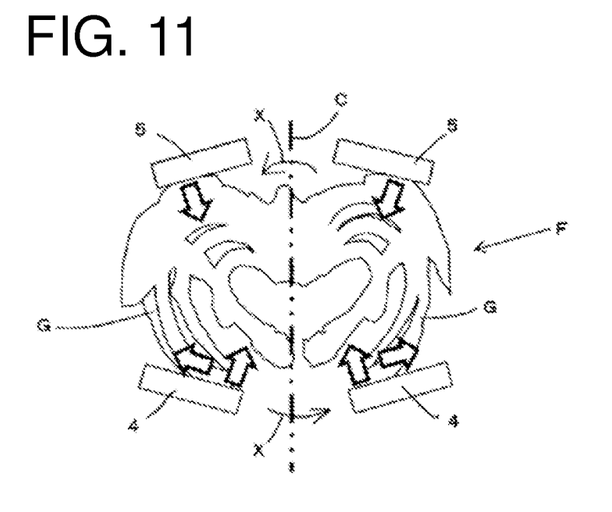
FIG. 11 depicts an explanatory drawing showing thoracic asymmetry corrected by the thorax front compression parts and the thorax rear compression parts (schematic plan view).

As shown in FIG. 11, if the lower part of the thorax F is asymmetrically twisted in an X direction with respect to the center line C by a thoracic vertebrae, a cause of lower-back pain, in other words, if the lower part of the thorax F has asymmetry or if a routine exercise is performed to move the lower part of the thorax F upward with the upper part of the thorax F, the thorax front compression parts 4 press the right and left thorax F from the front side so as to guide a smooth lateral extension of the thorax F, laterally extending the thorax F from an asymmetric state to a symmetric state. Furthermore, the thorax rear compression parts 5 press the rear sides of the right and left ribs G inward so as to guide a lateral extension of the front sides of the ribs G, extending the thorax F from an asymmetric state to a symmetric state. When the upper part R1 of the thorax F is moved upward by aspiration, arm swinging, and so on, the symmetric thorax F laterally opens the lower part R2. This prevents the application of a load to the pelvis A or the lumbar vertebrae so as to correct the posture.

One or a combination of at least two of the four compression parts is selected: the innominate front compression part 2 capable of abutting the abdominal part near the front side of the right or left innominate B, the innominate rear compression part 3 capable of abutting the pelvis near the rear side of the right or left innominate B, the thorax front compression part 4 capable of abutting the vicinity of the front side of the right or left thorax F, and the thorax rear compression part 5 capable of abutting the vicinity of the rear side of the lower part of the right or left thorax F. Therefore, a proper correction can be made depending upon the asymmetric parts, e.g., the asymmetric innominates B or the asymmetric lower part of the thorax F and the progression of the condition. A maximum correction force is obtained when the innominate front compression part 2, the innominate rear compression part 3, the thorax front compression part 4, and the thorax rear compression part 5 are attached to the body.

The belt winding mechanisms are vertically disposed at two points and are laterally disposed at two points, at four points in total. Therefore, the pressures of the innominate front compression parts 2, the innominate rear compression parts 3, the thorax front compression parts 4, and the thorax rear compression parts 5 on the body can be separately changed at the four points in the vertical and horizontal directions. This can more effectively correct asymmetry of the pelvis A and asymmetry of the thorax F when the pelvic asymmetry is caused by asymmetry of the innominate B and a displacement of the sacroiliac joint J or the asymmetry of the thorax F is caused by a twist of a thoracic vertebrae.

Moreover, a user with the attached posture corrective brace 1 can easily walk or perform exercises and so on. Therefore, a displacement of the sacroiliac joint J, i.e., asymmetry of the pelvis A can be effectively corrected by body movements and the pressures of the innominate front compression parts 2 and the innominate rear compression parts 3 on specific parts of the body according to the present invention. Furthermore, asymmetry of the lower part of the thorax F can be effectively corrected by movements such as aspiration, forward and backward bending, and arm swinging with the posture corrective brace 1 attached to the body and the pressures of the thorax front compression parts 4 and the thorax rear compression parts 5 on specific parts of the body according to the present invention. This can correct the posture of the body.

During movements such as walking and exercises with the posture corrective brace 1 attached to the body according to the present invention, the pressures of the innominate front compression parts 2, the innominate rear compression parts 3, the thorax front compression parts 4, or the thorax rear compression parts 5 may decrease. At this point, the belt winding mechanisms are rotated only at loosened points including the upper left, lower left, upper right, and lower right points on the innominate front compression parts 2, the innominate rear compression parts 3, the thorax front compression parts 4, and the thorax rear compression parts 5. Therefore, the fastening belts 9 on the body are fastened so as to increase the pressures, thereby effectively correcting asymmetry of the pelvis A or the lower part of the thorax F.

The posture corrective brace 1 has quite a small size and light weight and therefore can be carried with great ease. Moreover, a user can perform exercises with the posture corrective brace 1 attached to the body, achieving high usability.

The posture corrective brace 1 according to the second aspect of the present invention has the same effect as the invention according to the first aspect of the present invention. Moreover, the first belt winding mechanism 10 or the second belt winding mechanism 11 is detachably mounted on the front frame 7 and therefore can be attached to the body or detached from the body with great ease.

BRIEF DESCRIPTION OF THE DRAWINGS

For more thorough understanding of the present invention and advantages thereof, the following descriptions should be read in conjunction with the accompanying drawings, in which.

DESCRIPTION OF EMBODIMENTS OF THE INVENTION

As shown in FIGS. 3, 9, 11, and 12, the posture corrective brace 1 of the present invention includes a device attached to the body to correct asymmetry of the pelvis A while surrounding the circumference of the pelvis A of the body and/or a device attached to the body to correct asymmetry of the lower parts of thorax F while surrounding the circumference of the lower parts of the thorax F of the body, the posture corrective brace 1 including one or a combination of at least two of innominate front compression parts 2 capable of abutting abdominal parts near the front sides of the right and left innominates B, innominate rear compression parts 3 capable of abutting the pelvis near the rear sides of the right and left innominates B, thorax front compression parts 4 capable of abutting the vicinity of the front sides of the lower parts of the right and left thorax F, and thorax rear compression parts 5 capable of abutting the vicinity of the rear sides of the lower parts of the thorax F.

Therefore, the posture corrective brace 1 has 15 combinations: the innominate front compression part 2; the innominate rear compression part 3; the thorax front compression part 4; the thorax rear compression part 5; the innominate front compression part 2 and the innominate rear compression part 3; the innominate front compression part 2 and the thorax front compression part 4; the innominate front compression part 2 and the thorax rear compression part 5; the innominate rear compression part 3 and the thorax front compression part 4; the innominate rear compression part 3 and the thorax rear compression part 5; the thorax front compression part 4 and the thorax rear compression part 5; the innominate front compression part 2, the innominate rear compression part 3, and the thorax front compression part 4; the innominate front compression part 2, the innominate rear compression part 3, and the thorax rear compression part 5; the innominate front compression part 2, the thorax front compression part 4, and the thorax rear compression part 5; the innominate rear compression part 3, the thorax front compression part 4, and the thorax rear compression part 5; and the innominate front compression part 2, the innominate rear compression part 3, the thorax front compression part 4, and the thorax rear compression part 5.

The innominate front compression part 2 or the innominate rear compression part 3 have the effect of correcting asymmetry of the pelvis A, e.g., asymmetry of the innominates B in FIG. 8 and dislocation of a sacroiliac joint J. The thorax front compression part 4 or the thorax rear compression part 5 has the effect of correcting asymmetry of the lower part of the thorax F, e.g., asymmetry of ribs G in FIG. 11. If a single bone is slightly tilted, one of the compression parts is attached to the body, whereas if a single bone is more severely tilted or bones are tilted at multiple points, the compression parts are attached in combination to the body. The combination of the posture corrective brace 1 is preferably determined depending upon whether asymmetry is found near the pelvis A or the lower part of the thorax F, the displacement of a bone, and the amount of asymmetry.

Figure 12:
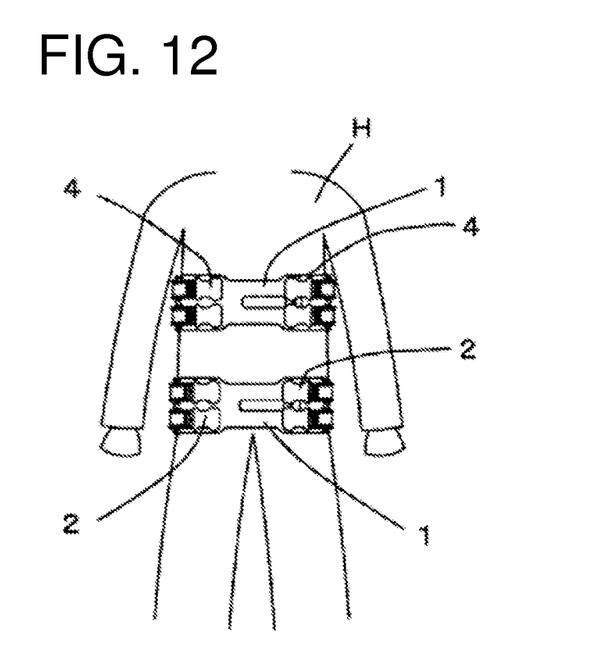
FIG. 12 depicts an explanatory drawing showing the posture corrective braces attached around the pelvis of a user and around the lower part of the thorax.

The posture corrective brace 1 of the present invention is small and lightweight in any combination and therefore is wearable on the body as shown in FIG. 12. Therefore, a user in a posture corrected by the attached posture corrective brace 1 can perform simple exercises such as arm swinging, forward and backward bending, stamping, walking, and squatting so as to learn exercise patterns of corrected joints in the muscles of the whole body and in the brain. This facilitates continuation of the correction effect.

The posture corrective brace 1 of the present invention includes a body brace 6 for attaching the innominate front compression part 2, the innominate rear compression part 3, the thorax front compression part 4, or the thorax rear compression part 5 around the circumference of the body. Two body braces 6 are used when covering two locations around the pelvis A of the body and the lower part of the thorax F of the body. A single body brace 6 is used when covering a location around the pelvis A of the body or the lower part of the thorax F of the body.

Figure 1:
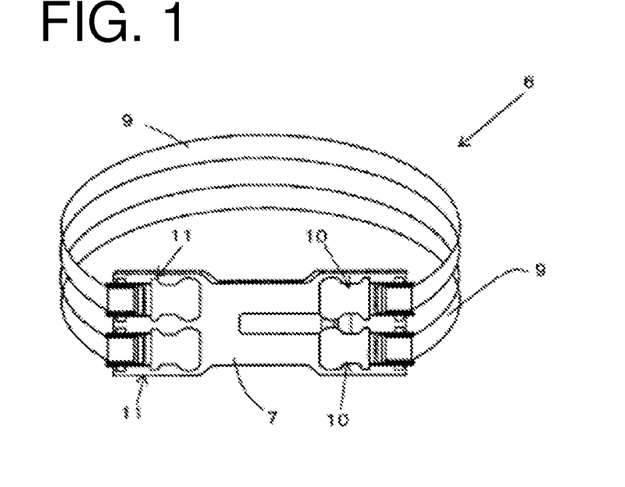
FIG. 1 depicts a schematic front view showing the body brace of a posture corrective brace according to the present invention.

As shown in FIG. 1, the body brace 6 includes a substantially belt-shaped front frame 7 laterally extended on an abdominal part at the front of the body or on the lower part of the thorax F, two first belt winding mechanisms 10 that are vertically disposed on the left end on the external side of the front frame 7, two second belt winding mechanisms 11 that are vertically disposed on the right end on the external side of the front frame 7, and two unstretchable fastening belts 9, each having one end fastened to the first belt winding mechanism 10 and the other end fastened to the second belt winding mechanism 11.

The front frame 7 capable of abutting the abdominal part at the front of the body or the lower part of the thorax F is belt-shaped in front view. The front frame 7 may have any shape, e.g., a linear shape, a circle, or a curve as long as the front frame 7 is belt-shaped in plan view. The front frame 7 is a thin plate made of nonferrous materials such as hard synthetic resin, hard rubber, and aluminum or rigid materials such as wood.

The two first belt winding mechanisms 10 and the two second belt winding mechanisms 11 are vertically disposed on both sides of the front frame 7. The four belt winding mechanisms operate in a separate manner. The first belt winding mechanism 10 and the second belt winding mechanism 11 may wind the fastening belt 9 by operating a handle in a ratchet mechanism, may wind the fastening belt 9 by rotating the handle and stop the fastening belt 9 with a stopper, or wind the fastening belt 9 with a hand and fasten the fastening belt 9 with a hook and loop fastener i.e. fabric tape. The belt winding mechanisms may have any structure as long as the fastening belt 9 can be wound.

Figure 2:
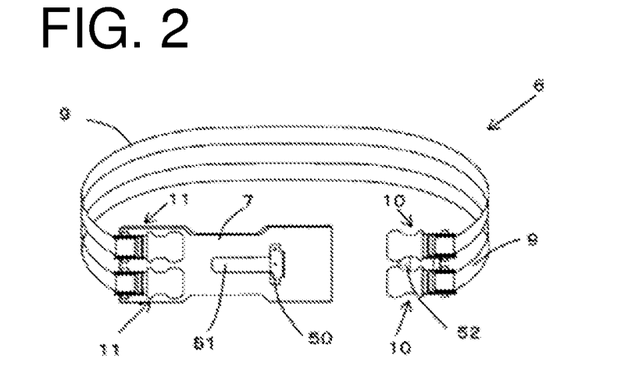
FIG. 2 depicts an explanatory drawing showing the body brace with one detached belt winding mechanism.

One of the first belt winding mechanism 10 and the second belt winding mechanism 11 is detachable from the front frame 7. For example, as shown in FIG. 2, first belt winding mechanisms 10 are attached to a mounting plate 52 detachably engaged with a locking protrusion 50 provided on the front frame 7, allowing the first belt winding mechanisms 10 to be detachable from the front frame 7. The detachable first belt winding mechanisms 10 allow the posture corrective brace 1 attached to the body to have a free end on one end of the fastening belt 9, facilitating attachment of the posture corrective brace 1 to the body.

Figure 5:
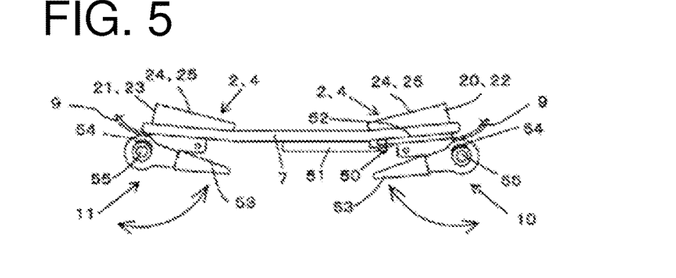
FIG. 5 depicts a schematic plan view showing a front frame with an attached innominate front compression part or an attached thorax front compression part.

A mechanism for winding the fastening belt 9 by operating a handle in a ratchet mechanism will be described below. As shown in FIG. 5, the first belt winding mechanism 10 and the two second belt winding mechanisms 11 each include a ratchet handle 53, a ratchet wheel 54 detachably engaged with the ratchet handle 53, and a ratchet that regulates the ratchet wheel 54 in one rotating direction. The ratchet handle 53 is pivoted about a support pin 55 with the ratchet handle 53 and the ratchet wheel 54 engage with each other, thereby rolling and fastening the wound fastening belt 9. Moreover, a release lever 51 disposed at the center of the front frame 7 is operated so as to simultaneously disengage the ratchets from all four ratchet wheels 54.

The fastening belts 9 will be described below. The two fastening belts 9 are vertically disposed with one end fastened to the respective first belt winding mechanisms 10 disposed in the vertical direction and the other end fastened to the respective second belt winding mechanism 11 disposed in the vertical direction. Moreover, if the innominate rear compression part 3 or the thorax rear compression part 5 is used, a substantially intermediate portion of the fastening belt 9 is inserted into the back frame 8. The intermediate portion is inserted through belt insertion portions 36 that are formed on both ends of the outer surface of the back frame 8 so as to allow the insertion of the fastening belt 9. The fastening belt 9 may be any one of a vegetable fiber belt, a synthetic fiber belt, a leather belt, or an alamido fiber belt as long as the belt is hardly stretchable by the winding force of the belt winding mechanism while the posture corrective brace 1 is attached to the body.

The innominate front compression part 2, the innominate rear compression part 3, the thorax front compression part 4, and the thorax rear compression part 5 will be described below.

Figure 3:
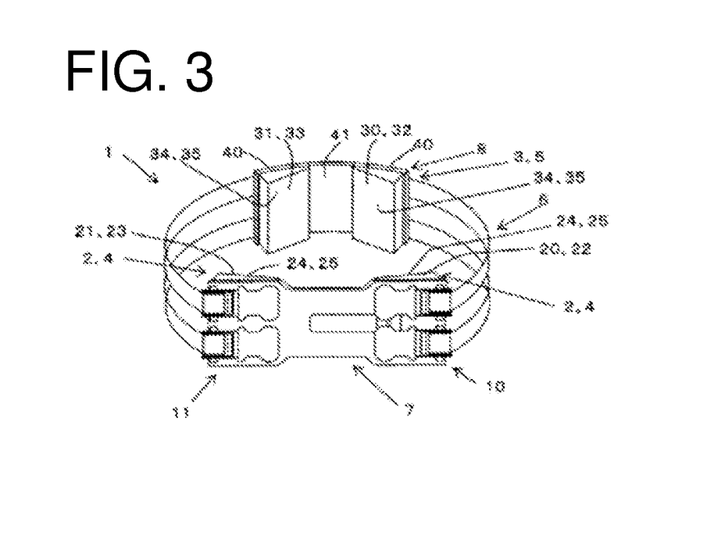
FIG. 3 depicts a schematic diagram showing the posture corrective brace from the front with front and rear compression parts attached to the single body brace.

First, the innominate front compression part 2 will be described below. As shown in FIGS. 3 and 5, the innominate front compression part 2 includes a first front pad 20 and a second front pad 21. The first front pad 20 is disposed on the left end of the body contact side of the front frame 7 while the second front pad 21 is disposed on the right end of the body contact side of the front frame 7. The first front pad 20 and the second front pad 21 are so large as to compress at least the right and left innominates B in front view. For example, the front pads are shaped like rectangles, polygons, or ovals. An inclined surface 24 has one end inclined to the body from the center of the front frame 7 in plan view. The body contact surfaces of the first and second front pads 20 and 21 form the inclined surfaces 24 that press the front sides of the right and left innominates B so as to guide the innominates B from the forward external side to the backward central side. The inclined surfaces 24 are made of materials including glass-containing resin, synthetic resin, and rubber that are so elastic as to prevent pain on the bones under compression and are hard enough to compress the bones.

The body contact surfaces of the first and second front pads 20 and 21 form the inclined surfaces 24 that press the front sides of the right and left innominates B so as to guide the innominates B from the forward external side to the backward central side. Therefore, the inclined surfaces 24 of the first front pad 20 and the second front pad 21 easily press protrusions on the front sides of the right and left innominates B from the front to the rear, eliminating displacement of the sacroiliac joint J so as to correct asymmetry of the pelvis A.

Figure 4:
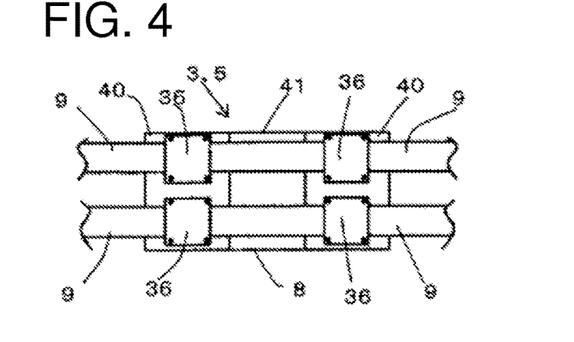
FIG. 4 depicts a schematic rear view of the posture corrective brace with innominate or thorax rear compression parts attached to the body brace.
Figure 6:
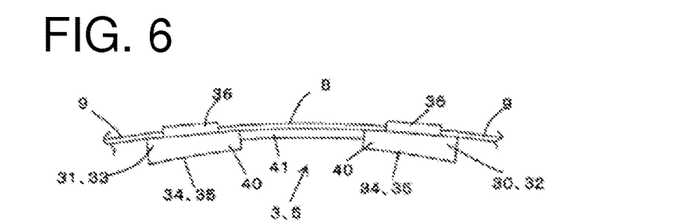
FIG. 6 depicts a schematic plan view showing a back frame with an attached innominate rear compression part or an attached thorax rear compression part.

The innominate rear compression part 3 will be described below. As shown in FIGS. 3, 4, and 6, the innominate rear compression part 3 includes the back frame 8 laterally extended so as to compress at least the right and left sacroiliac joints J, a first back pad 30 disposed on the left end of the back frame 8 on the internal side thereof and a second back pad 31 disposed on the right end of the back frame 8 on the internal side thereof, and the belt insertion portions 36, allowing the two fastening belts 9 to be inserted thereinto vertically and separately, disposed at positions on the back frame 8 on the external side thereof interposed between the first back pad 30 and the second back pad 31 disposed on the back frame 8 on the internal side thereof, i.e., on the body contact side of the back frame 8.

The back frame 8 is shaped like a belt abutting the rear side of the body in front view. The back frame 8 includes right and left side portions 40 and a central portion 41. The shapes of the right and left side portions 40 are not limited and may be linear or circular in plan view. The side portions 40 are thin plates made of nonferrous materials such as hard synthetic resin, hard rubber, and aluminum or rigid materials such as wood. The central portion 41 is shaped like a belt in front view and is made of a flexible material. The back frame 8 may be an integral type including the right and left side portions 40 and the central portion 41 or a divided type including the right and left side portions 40 without the central portion 41. Since the central portion 41 is flexible, the right and left side portions 40 easily follow any change in the curved surface on the circumference of the body.

The first back pad 30 is disposed on the left end of the body contact side of the back frame 8 while the second back pad 31 is disposed on the right end of the body contact side of the back frame 8. The first back pad 30 and the second back pad 31 are so large as to compress at least one of the right and left sacroiliac joints J in front view. For example, the back pads are shaped like rectangles, polygons, or ovals. An inclined surface 34 has one end inclined to the body from the center of the back frame 8 in plan view. The body contact surfaces of the first and second back pads 30 and 31 form the inclined surfaces 34 that press the rear sides of the right and left innominates B so as to guide the innominates B from the forward external side to the backward central side. The inclined surfaces 34 are made of materials including glass-containing resin, synthetic resin, and rubber that are so elastic as to prevent pain on the bones under compression and are hard enough to compress the bones.

The body contact surfaces of the first and second back pads 30 and 31 form the inclined surfaces 34 that press the rear sides of the right and left innominates B so as to guide the innominates B from the backward external side to the central side. Therefore, the inclined surfaces 34 of the first back pad 30 and the second back pad 31 easily press the rear sides of the right and left innominates B diagonally from the rear side of the body toward the sacrum S that is the center of the body. The sacroiliac joints J are compressed so as to be suitable with symmetry. This eliminates displacement of the sacroiliac joint J so as to correct asymmetry of the pelvis A.

The thorax front compression part 4 will be described below. As shown in FIGS. 3 and 5, the thorax front compression part 4 includes a third front pad 22 and a fourth front pad 23. The third front pad 22 is disposed on the left end of the body contact side of the front frame 7 while the fourth front pad 23 is disposed on the right end of the body contact side of the front frame 7. The third front pad 22 and the fourth front pad 23 are so large as to compress at least the front sides of the lower parts of the right and left thorax F in front view. For example, the front pads are shaped like rectangles, polygons, or ovals. An inclined surface 25 has one end inclined to the body from the center of the front frame 7 in plan view. The body contact surfaces of the third and fourth front pads 22 and 23 form the inclined surfaces 25 that press the front sides of the right and left ribs G so as to guide the lateral extension of the ribs G from the front. The inclined surfaces 25 are made of materials including glass-containing resin, synthetic resin, and rubber that are so elastic as to prevent pain on the bones under compression and are hard enough to compress the bones.

The body contact surfaces of the third and fourth front pads 22 and 23 form the inclined surfaces 25 that press the front sides of the right and left ribs G so as to guide a lateral extension of the ribs G from the front. Therefore, the inclined surfaces 25 of the third front pad 22 and the fourth front pad 23 easily extend protrusions to the right and left on the front sides of the ribs G at the lower parts of the right and left thorax F, eliminating asymmetry of the lower parts of the thorax F so as to correct asymmetry of the lower parts of the thorax F.

The thorax rear compression part 5 will be described below. As shown in FIGS. 3 and 6, the thorax rear compression part 5 includes the back frame 8 laterally extended so as to compress at least the rear of the lower parts of the right and left thorax F, a third back pad 32 disposed on the left end of the back frame 8 on the internal side thereof, i.e., on the body side of the back frame 8 and a fourth back pad 33 disposed on the right end of the back frame 8 on the internal side thereof, and the belt insertion portions 36 allowing the two fastening belts 9 to be inserted thereinto vertically and separately, disposed at positions on the back frame 8 on the external side thereof interposed between the third back pad 32 and the fourth back pad 33 disposed on the back frame 8 on the internal side thereof, i.e., on the body side of the back frame 8.

The back frame 8 is shaped like a belt in abutting the rear side of the body in front view. The back frame 8 includes the right and left side portions 40 and the central portion 41. The shapes of the right and left side portions 40 are not limited and may be linear or circular in plan view. The side portions 40 are thin plates made of nonferrous materials such as hard synthetic resin, hard rubber, and aluminum or rigid materials such as wood. The central portion 41 is shaped like a belt in the front view and is made of a flexible material. The back frame 8 may be an integral type including the right and left side portions 40 and the central portion 41 or a divided type including the right and left side portions 40 without the central portion 41. Since the central portion 41 is flexible, the right and left side portions 40 easily follow any change in the curved surface on the circumference of the body.

The third back pad 32 is disposed on the left end of the body contact side of the back frame 8 while the fourth back pad 33 is disposed on the right end of the body contact side of the back frame 8. The third back pad 32 and the fourth back pad 33 are so large as to compress at least the rear of the lower parts of the right and left thorax F in front view. For example, the back pads are shaped like rectangles, polygons, or ovals. An inclined surface 35 has one end inclined to the body from the center of the back frame 8 in plan view. The body contact surfaces of the third and fourth front pads 32 and 33 form the inclined surfaces 35 that press the rear sides of the right and left ribs G so as to guide the lateral extension of the rear sides of the ribs G. The inclined surfaces 35 are made of materials including glass-containing resin, synthetic resin, and rubber that are so elastic as to prevent pain on the bones under compression and are hard enough to compress the bones.

The body contact surfaces of the third and fourth back pads 32 and 33 form the inclined surfaces 35 that press the rear sides of the right and left ribs G so as to guide lateral extension of the ribs G from the front. The rear side of the lower part of the thorax F is pressed inward so as to laterally extend the front sides of the ribs G, eliminating asymmetry of the lower part of the thorax F so as to correct asymmetry of the lower part of the thorax F.

The relationship between the body brace 6 to be wrapped around the body and the innominate front compression part 2, the innominate rear compression part 3, the thorax front compression part 4, and the thorax rear compression part 5 will be described below. The innominate front compression part 2, the innominate rear compression part 3, the thorax front compression part 4, and the thorax rear compression part 5 are combined in the posture corrective brace 1. In the case of combinations of other compressing parts, the compressing parts are combined like the actions of the respective compressing parts.

The innominate front compression part 2 and the innominate rear compression part 3 that are attached to the body so as to surround the circumference of the pelvis A of the body will be first described below. When the upper fastening belt 9 of the first belt winding mechanism 10 is operated in a winding direction, the upper sides of the first front pad 20 and the first back pad 30 on the left side of the body can first fasten the body. When the lower fastening belt 9 of the first belt winding mechanism 10 is operated in the winding direction, the lower sides of the first front pad 20 and the first back pad 30 can first fasten the body. When the upper fastening belt 9 of the second belt winding mechanism 11 is operated in the winding direction, the upper sides of the second front pad 21 and the second back pad 31 on the right side of the body can first fasten the body. When the lower fastening belt 9 of the second belt winding mechanism 11 is operated in the winding direction, the lower sides of the second front pad 21 and the second back pad 31 on the right side of the body can first fasten the body.

Therefore, when the innominate front compression part 2 and the innominate rear compression part 3 are attached to the body, the pressures of the first front pad 20, the second front pad 21, the first back pad 30, and the second back pad 31 to the body can be freely adjusted. Moreover, when loosening is felt during simple exercises such as stomping, walking, and squatting with the innominate front compression part 2 and the innominate rear compression part 3 attached to the body, the pressure can be adjusted only on the part where the loosening is felt. This can always apply any degree of pressure to the body, easily eliminating displacement of the sacroiliac joint J and asymmetry of the pelvis A.

The thorax front compression part 4 and the thorax rear compression part 5 that wrap around the body so as to surround the circumference of the lower part of the thorax F of the body will be described below. When the upper fastening belt 9 of the first belt winding mechanism 10 is operated in the winding direction, the upper sides of the third front pad 22 and the third back pad 32 on the left side of the body can first fasten the body. When the lower fastening belt 9 of the first belt winding mechanism 10 is operated in the winding direction, the lower sides of the third front pad 22 and the third back pad 32 on the left side of the body can first fasten the body. When the upper fastening belt 9 of the second belt winding mechanism 11 is operated in the winding direction, the upper sides of the fourth front pad 23 and the fourth back pad 33 on the right side of the body can first fasten the body. When the lower fastening belt 9 of the second belt winding mechanism 11 is operated in the winding direction, the lower sides of the fourth front pad 23 and the fourth back pad 33 on the right side of the body can first fasten the body.

Therefore, when the thorax front compression part 4 and the thorax rear compression part 5 are attached to the body, the pressures of the third front pad 22, the fourth front pad 23, the third back pad 32, and the fourth back pad 33 to the body can be freely adjusted. Moreover, when loosening is felt during simple exercises such as breathing, right and left bending, or arm swinging with the thorax front compression part 4 and the thorax rear compression part 5 attached to the body, the pressure can be adjusted only on the part where the loosening is felt. This can always apply any degree of pressure to the body, easily eliminating asymmetry of the ribs G and asymmetry of the lower part of the thorax F.

The posture corrective brace 1 as one of the present embodiments can be used as follows: simple exercises such as stamping, walking, and squatting are performed while correcting asymmetry of bones with the posture corrective brace 1, and therefore exercise patterns having no asymmetry of bones and joints can be easily learned in the brain and in the muscles of the whole body. In the following posture corrective brace 1, the belt winding mechanism with a ratchet mechanism includes a combination of the innominate front compression part 2, the innominate rear compression part 3, the thorax front compression part 4, and the thorax rear compression part 5.

Figure 9:
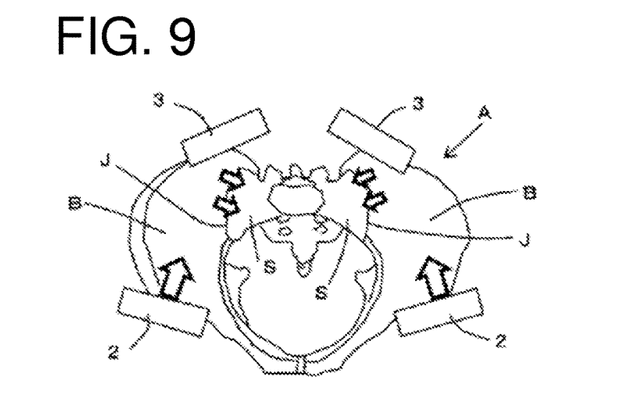
FIG. 9 depicts an explanatory drawing showing pelvic asymmetry corrected by the innominate front compression parts and the innominate rear compression parts (schematic plan view).

First, referring to FIGS. 3 and 9, a method of wrapping the posture corrective brace 1 around the circumference of the pelvis A of the body will be described below. The posture corrective brace 1 includes the attached innominate front compression part 2 and innominate rear compression part 3.

First, the first belt winding mechanisms 10 are detached from the front frame 7 at the mounting plate 52. In this state, the front frame 7 is disposed on the front side of the body, the fastening belts 9 are wrapped from the back side to the front side, and then the mounting plate 52 combined with the first belt winding mechanisms 10 is engaged with the locking protrusion 50 so as to be attached to the front frame 7. The back frame 8 in this state is located on the back side of the body.

Subsequently, the ratchet handles 53 of the two first belt winding mechanisms 10 and the two second belt winding mechanisms 11 are suitably operated to fasten the two fastening belts 9. Therefore, the first front pad 20 of the front frame 7 presses the front end of the left side of the left innominate B toward the sacrum 5; meanwhile, the second front pad 21 presses the front end of the right side of the right innominate B toward the sacrum S. At this point, the first front pad 20 and the second front pad 21 each include the inclined surface 24 and therefore can effectively press the right and left innominates B toward the sacrum S.

In this state, the back frame 8 is in abutting the back of the body, the first back pad 30 presses the rear end of the left innominate B toward the sacrum S, and the second back pad 31 presses the rear end of the right innominate B toward the sacrum S. At this point, the first back pad 30 and the second back pad 31 each include the inclined surface 34 and therefore can effectively press the right and left innominates B toward the sacrum S.

Referring to FIGS. 3, 10, 11, etc., a method of wrapping the posture corrective brace 1 around the body so as to surround the circumference of the lower part of the thorax F of the body will be described below. The posture corrective brace 1 includes the thorax front compression part 4 and the thorax rear compression part 5.

First, the first belt winding mechanism 10 is detached from the front frame 7 at the mounting plate 52. In this state, the front frame 7 is disposed on the front side of the body, the fastening belts 9 are wrapped from the back side to the front side, and then the mounting plate 52 combined with the first belt winding mechanisms 10 is engaged with the locking protrusion 50 so as to be attached to the front frame 7. The back frame 8 in this state is located on the back side of the body. As shown in FIG. 10, the posture corrective brace 1 is attached to the body at lower part R2 of the thorax F.

Subsequently, the ratchet handles 53 of the two first belt winding mechanisms 10 and the two second belt winding mechanisms 11 are suitably operated to fasten the two fastening belts 9. Therefore, the third front pad 22 of the front frame 7 presses the left ribs G so as to laterally extend the ribs G; meanwhile, the fourth front pad 23 presses the right ribs G so as to laterally extend the ribs G. At this point, the third front pad 22 and the fourth front pad 23 each include the inclined surface 25 and therefore can effectively press the right and left ribs G so as to laterally extend the ribs G.

In this state, the back frame 8 is abutting the back of the body, the third back pad 32 presses the rear end of the lower part of the left thorax F so as to extend the lower part of the thorax F on the front side, and the fourth back pad 33 presses the rear end of the lower part of the right thorax F so as to extend the lower part of the right thorax F on the front side. At this point, the third back pad 32 and the fourth back pad 33 each include the inclined surface 35 and therefore can effectively press the thorax F so as to laterally extend the front sides of the lower parts of the right and left thorax F.

As shown in FIG. 12, at the completion of attachment to a user H, the user H performs light exercises such as walking, stamping, squatting and exercises using the part above the thorax F, e.g., aspiration, forward and backward bending, and arm swinging.

Light exercises such as walking, stamping, and squatting press the front of the sacrum S rearward. This laterally presses the rear of the sacrum S from the outside to the center so as to correct an asymmetric state of the sacrum S to a symmetric state. Therefore, displacement of the sacroiliac joint J and asymmetry of the pelvis A are both eliminated.

Moreover, exercises such as aspiration, forward and backward bending, and arm swinging laterally extend the lower part of the thorax F. This moves upper part R1 of the thorax F in FIG. 10 upward but does not move the lower part R2 of the thorax F upward because the lower part R2 is fastened by the third and fourth front pads 22 and 23. This corrects asymmetry of the ribs G and eliminates asymmetry of the thorax F.

Furthermore, if the fastening belt 9 is loosened during an operation, the fastening belt 9 is fastened by the first belt winding mechanism 10 and the second belt winding mechanism 11. Specifically, the fastening belt 9 moves in a fastened state and is fastened in a loosened state, correcting asymmetry of the pelvis A and the lower part of the thorax F.

Asymmetry is preferably corrected by the posture corrective brace 1 for about ten minutes at a time, twice or three times in a week. Typically, posture is improved by one or two times of correction.

| (Reference Numerals) | |
|---|---|
| 1 posture corrective brace | 2 innominate front compression part |
| 3 innominate rear compression part | 4 thorax front compression part |
| 5 thorax rear compression part | 6 body brace |
| 7 front frame | 8 back frame |
| 9 fastening belt | 10 first belt winding mechanism |
| 11 second belt winding mechanism | 20 first front pad |
| 21 second front pad | 22 third front pad |
| 23 fourth front pad | 24 inclined surface |
| 25 inclined surface | 30 first back pad |
| 31 second back pad | 32 third back pad |
| 33 fourth back pad | 34 inclined surface |
| 35 inclined surface | 36 belt insertion portion |
| 40 side portion | 41 central portion |
| 50 locking protrusion | 51 release lever |
| 52 mounting plate | 53 ratchet handle |
| 54 ratchet wheel | 55 support pin |
| The pelvis | B innominate |
| S sacrum | J sacroiliac joint |
| F thorax | G rib |
| R1 upper part | R2 lower part |

What is claimed is:

1. A posture corrective brace including a device for correcting asymmetry of the pelvis configured to be attached to a body such that the device surrounds the circumference of the pelvis of the body, the posture corrective brace comprising:

an innominate front compression part capable of abutting an abdominal part near the front side of the right or left innominate, and an innominate rear compression part capable of abutting the pelvis near the rear side of the right or left innominate; and at least one body brace configured to be attached to the body such that the at least one body brace surrounds the circumference of the pelvis of the body, the at least one body brace including a front frame in a substantially belt-like shape configured to be laterally extended on the abdominal part of the front side of the body, two first belt winding mechanisms vertically disposed on the left end of the front frame on the external side thereof, two second belt winding mechanisms vertically disposed on the right end of the front frame on the external side thereof, and two unstretchable fastening belts each having one end fastened to each of the two first belt winding mechanisms and the other end fastened to each of the two second belt winding mechanisms, wherein the innominate front compression part includes a first front pad disposed on the left end of the front frame on the internal side thereof and a second front pad disposed on the right end of the front frame on the internal side thereof, the first front pad and the second front pad having body contact surfaces each shaped as an inclined surface formed so as to press the front side of the right or left innominate such that the innominate can be guided from a forward external side to a backward central side, wherein the innominate rear compression part includes a back frame laterally extended so as to compress the rear of the right and left innominates, a first back pad disposed on the left end of the back frame on the internal side thereof, a second back pad disposed on the right end of the back frame on the internal side thereof, and belt insertion portions configured to allow the two fastening belts to be inserted thereinto vertically and separately, the belt insertion portions disposed at positions on the back frame on the external side thereof interposed between the first back pad and the second back pad, the two fastening belts being inserted into the belt insertion portions, the first back pad and the second back pad having body contact surfaces each shaped as an inclined surface formed so as to press the rear side of the right or left innominate such that the innominate can be guided from a backward external side to a central side, and wherein when in use, the body is fastened by the upper side of the first front pad and the upper side of the first back pad on the left side of the body, on a priority basis, when the upper fastening belt of the first belt winding mechanism out of the two fastening belts is operated in a winding direction;

the body is fastened by the lower side of the first front pad and the lower side of the first back pad on the left side of the body, on a priority basis, when the lower fastening belt of the first belt winding mechanism out of the two fastening belts is operated in a winding direction;

the body is fastened by the upper side of the second front pad and the upper side of the second back pad on the right side of the body, on a priority basis, when the upper fastening belt of the second belt winding mechanism out of the two fastening belts is operated in a winding direction; and the body is fastened by the lower side of the second front pad and the lower side of the second back pad on the right side of the body, on a priority basis, when the lower fastening belt of the second belt winding mechanism out of the two fastening belts is operated in a winding direction.

2. The posture corrective brace according to claim 1, wherein the first belt winding mechanism or the second belt winding mechanism is detachably mounted on the front frame.

3. A posture corrective brace including a device for correcting asymmetry of a lower part of the thorax configured to be attached to a body such that the device surrounds the circumference of the lower part of the thorax of the body, the posture corrective brace comprising:

a thorax front compression part capable of abutting the vicinity of the front side of the lower part of the right or left thorax, and a thorax rear compression part capable of abutting the vicinity of the rear side of the lower part of the right or left thorax; and at least one body brace configured to be attached to the body such that the at least one body brace surrounds the circumference of the lower part of the thorax of the body, the at least one body brace including a front frame in a substantially belt-like shape configured to be laterally extended on the lower part of the thorax of the front side of the body, two first belt winding mechanisms vertically disposed on the left end of the front frame on the external side thereof, two second belt winding mechanisms vertically disposed on the right end of the front frame on the external side thereof, and two unstretchable fastening belts each having one end fastened to each of the two first belt winding mechanisms and the other end fastened to each of the two second belt winding mechanisms, wherein the thorax front compression part includes a third front pad disposed on the left end of the front frame on the internal side thereof and a fourth front pad disposed on the right end of the front frame on the internal side thereof, the third front pad and the fourth front pad having body contact surfaces each shaped as an inclined surface formed so as to press the front side of the right or left rib such that the rib can be guided from a forward side position to a laterally-extended side position, wherein the thorax rear compression part includes a back frame laterally extended so as to compress the rear of the right and left ribs, a third back pad disposed on the left end of the back frame on the internal side thereof, a fourth back pad disposed on the right end of the back frame on the internal side thereof, and belt insertion portions configured to allow the two fastening belts to be inserted thereinto vertically and separately, the belt insertion portions disposed at positions on the back frame on the external side thereof interposed between the third back pad and the fourth back pad, the two fastening belts being inserted into the belt insertion portions, the third back pad and the fourth back pad having body contact surfaces each shaped as an inclined surface formed so as to press the rear sides of the right and left ribs inward such that the front sides of the ribs can be extended laterally, and wherein when in use, the body is fastened by the upper side of the third front pad and the upper side of the third back pad on the left side of the body, on a priority basis, when the upper fastening belt of the first belt winding mechanism out of the two fastening belts is operated in a winding direction;

the body is fastened by the lower side of the third front pad and the lower side of the third back pad on the left side of the body, on a priority basis, when the lower fastening belt of the first belt winding mechanism out of the two fastening belts is operated in a winding direction;

the body is fastened by the upper side of the fourth front pad and the upper side of the fourth back pad on the right side of the body, on a priority basis, when the upper fastening belt of the second belt winding mechanism out of the two fastening belts is operated in a winding direction; and the body is fastened by the lower side of the fourth front pad and the lower side of the fourth back pad on the right side of the body, on a priority basis, when the lower fastening belt of the second belt winding mechanism out of the two fastening belts is operated in a winding direction.

4. The posture corrective brace according to claim 3, wherein the first belt winding mechanism or the second belt winding mechanism is detachably mounted on the front frame.

5. A posture corrective brace including a device for correcting asymmetry of the pelvis configured to be attached to a body such that the device surrounds the circumference of the pelvis of the body, the posture corrective brace comprising:

an innominate front compression part capable of abutting an abdominal part near the front side of the right or left innominate; and at least one body brace configured to be attached to the body such that the at least one body brace surrounds the circumference of the pelvis of the body, the at least one body brace including a front frame in a substantially belt-like shape configured to be laterally extended on the abdominal part of the front side of the body, two first belt winding mechanisms vertically disposed on the left end of the front frame on the external side thereof, two second belt winding mechanisms vertically disposed on the right end of the front frame on the external side thereof, and two unstretchable fastening belts each having one end fastened to each of the two first belt winding mechanisms and the other end fastened to each of the two second belt winding mechanisms, wherein the innominate front compression part includes a first front pad disposed on the left end of the front frame on the internal side thereof and a second front pad disposed on the right end of the front frame on the internal side thereof, the first front pad and the second front pad having body contact surfaces each shaped as an inclined surface formed so as to press the front side of the right or left innominate such that the innominate can be guided from a forward external side to a backward central side, and wherein when in use, the body is fastened by the upper side of the first front pad on the left side of the body, on a priority basis, when the upper fastening belt of the first belt winding mechanism out of the two fastening belts is operated in a winding direction;

the body is fastened by the lower side of the first front pad on the left side of the body, on a priority basis, when the lower fastening belt of the first belt winding mechanism out of the two fastening belts is operated in a winding direction;

the body is fastened by the upper side of the second front pad on the right side of the body, on a priority basis, when the upper fastening belt of the second belt winding mechanism out of the two fastening belts is operated in a winding direction; and the body is fastened by the lower side of the second front pad on the right side of the body, on a priority basis, when the lower fastening belt of the second belt winding mechanism out of the two fastening belts is operated in a winding direction.

6. The posture corrective brace according to claim 5, wherein the first belt winding mechanism or the second belt winding mechanism is detachably mounted on the front frame.

7. A posture corrective brace including a device for correcting asymmetry of a lower part of the thorax configured to be attached to a body such that the device surrounds the circumference of the lower part of the thorax of the body, the posture corrective brace comprising:

a thorax front compression part capable of abutting the vicinity of the front side of the lower part of the right or left thorax; and at least one body brace attached to the body such that the at least one body brace surrounds the circumference of the body, the at least one body brace including a front frame in a substantially belt-like shape configured to be laterally extended on the lower part of the thorax of the front side of the body, two first belt winding mechanisms vertically disposed on the left end of the front frame on the external side thereof, two second belt winding mechanisms vertically disposed on the right end of the front frame on the external side thereof, and two unstretchable fastening belts each having one end fastened to each of the two first belt winding mechanisms and the other end fastened to each of the two second belt winding mechanisms, wherein the thorax front compression part includes a third front pad disposed on the left end of the front frame on the internal side thereof and a fourth front pad disposed on the right end of the front frame on the internal side thereof, the third front pad and the fourth front pad having body contact surfaces each shaped as an inclined surface formed so as to press the front side of the right or left rib such that the rib can be guided from a forward side position to a laterally-extended side position, and wherein when in use, the body is fastened by the upper side of the third front pad on the left side of the body, on a priority basis, when the upper fastening belt of the first belt winding mechanism out of the two fastening belts is operated in a winding direction;

the body is fastened by the lower side of the third front pad on the left side of the body, on a priority basis, when the lower fastening belt of the first belt winding mechanism out of the two fastening belts is operated in a winding direction;

the body is fastened by the upper side of the fourth front pad on the right side of the body, on a priority basis, when the upper fastening belt of the second belt winding mechanism out of the two fastening belts is operated in a winding direction; and the body is fastened by the lower side of the fourth front pad on the right side of the body, on a priority basis, when the lower fastening belt of the second belt winding mechanism out of the two fastening belts is operated in a winding direction.

8. The posture corrective brace according to claim 7, wherein the first belt winding mechanism or the second belt winding mechanism is detachably mounted on the front frame.

* * * * *